(12) United States Patent
Pines

(10) Patent No.: US 8,375,954 B2
(45) Date of Patent: Feb. 19, 2013

(54) DEVICE AND METHOD FOR RESTRAINING FOOD INTAKE

(75) Inventor: Erella Pines, Pardes Hannah (IL)

(73) Assignee: Nobesity Ltd., Haifa (IL)

( * ) Notice: Subject to any disclaimer, the term of this patent is extended or adjusted under 35 U.S.C. 154(b) by 172 days.

(21) Appl. No.: 12/808,364

(22) PCT Filed: Dec. 22, 2008

(86) PCT No.: PCT/IL2008/001653
§ 371 (c)(1),
(2), (4) Date: Jun. 15, 2010

(87) PCT Pub. No.: WO2009/081401
PCT Pub. Date: Jul. 2, 2009

(65) Prior Publication Data
US 2010/0288287 A1    Nov. 18, 2010

(30) Foreign Application Priority Data
Dec. 26, 2007  (IL) .......................................... 188435

(51) Int. Cl.
*A61F 5/37* (2006.01)
*A61C 17/00* (2006.01)
(52) U.S. Cl. ........................................ 128/846; 433/80
(58) Field of Classification Search ............... 433/18, 433/23, 19, 215, 6, 9, 25, 80; 128/897, 848, 128/898; 600/300, 23, 24; 434/127, 262, 434/263; 601/38
See application file for complete search history.

(56) References Cited

U.S. PATENT DOCUMENTS

| | | |
|---|---|---|
| 3,475,818 A | 11/1969 | Abrams |
| 4,001,940 A | 1/1977 | Cusato |
| 4,127,940 A | 12/1978 | Shilliday |
| 4,202,328 A | 5/1980 | Sukkarie |
| 4,218,611 A | 8/1980 | Cannon |
| 4,471,771 A | 9/1984 | Steven et al. |
| 4,472,137 A | 9/1984 | Barone |
| 4,512,739 A | 4/1985 | Kaniadakis |
| 4,825,881 A | 5/1989 | Bessler |
| 4,968,248 A | 11/1990 | McColgan et al. |

(Continued)

FOREIGN PATENT DOCUMENTS

ES 2164570 2/2002

OTHER PUBLICATIONS

International Search Report mailed Jun. 18, 2009, in International Application No. PCT/IL2008/001653, filed Dec. 22, 2008.

(Continued)

*Primary Examiner* — Loan Thanh
*Assistant Examiner* — Tarla Patel
(74) *Attorney, Agent, or Firm* — Hershkovitz & Associates LLC; Abraham Hershkovitz

(57) ABSTRACT

The present invention relates to intra oral devices for treating overweight and obesity by reducing and/or limiting the mouth opening "and/or slowing down the rate of chewing and more specifically to such devices handled by the user with or without the need for professional help, a method and use thereof. Said intra oral device of the present invention consists of a restraining device (8) which is being anchored in the upper and lower jaws, consisting of an elastic element which is inserted into two respective inter-proximal spaces (IPSs) of said upper and said lower jaws and reduces and/or limits the mouth opening and/or slows down the rate of chewing.

23 Claims, 6 Drawing Sheets

U.S. PATENT DOCUMENTS

| | | | |
|---|---|---|---|
| 5,575,643 A | 11/1996 | Green | |
| 6,138,679 A * | 10/2000 | Renders et al. | 128/897 |
| 2003/0075186 A1* | 4/2003 | Florman | 128/869 |
| 2009/0148812 A1* | 6/2009 | Pines | 433/80 |
| 2010/0192972 A1* | 8/2010 | Kazes | 132/322 |

OTHER PUBLICATIONS

International Preliminary Report on Patentability mailed Jul. 8, 2010 in PCT/IL2008/001653, filed Dec. 22, 2008.

* cited by examiner

DEVICE AND METHOD FOR RESTRAINING FOOD INTAKE

TECHNICAL FIELD OF THE INVENTION

The present invention relates to intra oral devices for treating overweight and obesity by reducing and/or limiting the mouth opening and/or slowing down the rate of chewing and more specifically to such devices handled by the user with or without the need for professional help, a method and use thereof.

BACKGROUND OF THE INVENTION

Overweight and obesity are some of the most common health and social problems. Millions of people suffer from overweight, which is considered to be a main cause for diseases and early death. In developed countries obesity is becoming a national public health problem because no single treatment is available for treating the condition satisfactorily. The International Health Organization refers to overweight as an epidemic, and has formed a special task force to treat one of the biggest risks threatening human health.

Overweight occurs when there is an excess of energy consumption in relation to energy release. The cause for overweight differ from patient to patient, and it is commonly believed to be associated with several genetic, psychological, social, behavioral and environmental factors.

People who suffer from overweight tend to belong to risk groups prone to stress, obesity associated disorders, heart attacks, diabetes, strokes, gall bladder diseases, sleep death, respiratory problems and depression. The goals of overweight treatment are to reduce the risks of developing related disease or the aggravation of existing ones, to lengthen life expectancy and to improve the way and quality of life. Treating overweight usually involves diets, psychological treatments, psychiatric treatments, and use of drugs, alternative medicine, physical activity and surgical intervention. The challenge of treating moderate obesity is to find an effective approach which is effective in maintaining reduced weight because after weight reduction, people are often prone to regain the weight. This is where behavioral therapy is effective.

In recent years researchers have reached the conclusion that the most successful approach for the treatment of obesity is a multi-disciplinary one. To succeed in the long term, a combination of behavioral therapy (changing eating habits) and other treatments is required. According to the National Institutes of Health's Guide to Behavior Change, slowing the rate of eating to may allow satiety (fullness) signals to begin to be transmitted by the end of the meal. Recent studies show that dietary behavioral modifications and exercise are the most efficient methods for managing body weight. The present invention is related to a device designed to aid weight loss by controlling the amount of food a person bites and the rate of the mastication, e.g. reduces and/or limits the mouth opening and/or slows down the rate of chewing.

Slow and thorough chewing enables better and more complete absorption of the food in the stomach, and decreases the hunger feeling. To the contrary, fast eating promotes incomplete food absorption and encourages the eater to consume more in order to feel satiety. Another way to eat less and feel full is to give the brain time to get the message that the stomach is full. Because it takes 15 minutes or more to get the signal to the brain, eating slowly, as well as chewing and grinding slowly, are effective in this respect.

Oral devices and more specifically dental appliances have been used to control weight by slowing the rate of food mastication. The body is allowed time to respond to the ingestion of food with a sensation of satiety. The user is supposed to feel full after consuming a reduced amount of food. Therefore, the patient eats less and as a result he loses weight.

A number of dental appliances have been described as aiding a user in achieving weight loss through the restriction of mandibular movements.

For example, U.S. Pat. No. 4,471,771 discloses an oral weight control apparatus. The apparatus includes a guard apparatus, net, or other sieve-like blocking means secured in the mouth of the user. Liquids and finely ground material inside the mouth may freely pass through the guard or sieve but solid foods may not. In the preferred embodiment, the blocking means functions as a one way valve, blocking solid foods from entering the stomach through the mouth.

U.S. Pat. No. 4,825,881 discloses an apparatus for inhibiting the intake of food. The apparatus comprises first and second spaced adhesive strips applied above and below the upper and lower lips of the user which are interconnected by wires which provide relatively normal movement of the mouth to permit normal speech, while at the same time inhibiting, but not totally preventing the intake of solids and liquids.

is U.S. Pat. No. 6,138,679 discloses a mandibular restraint that includes a pain-inducing device. The pain-inducing device may be a bar shaped element with a thickened portion that is intended to press against the gums or jaws of the patient should the patient attempt to open the mouth beyond a threshold position. Alternatively, or additionally, the pain-inducing device delivers a painful electric shock to the gums or teeth of the patient.

US 2003/0075186 discloses a device for affixing the teeth of a user by engaging a plurality of individual teeth of the mandible with the opposite respective teeth of the maxilla. The affixation is carried out separately for each pair of teeth (upper and lower) involving the application of a resin to anchor an elastic element to the teeth.

US 2003/0059737 four frames are being secured to the upper and lower right and left dental arches and are connected to magnets on each frame.

ES 2164570 discloses a closing system for teeth. It consists of rings that are fixed to the teeth and a chain that will pass through the rings to close the teeth as much as possible and an electronic part.

U.S. Pat. No. 4,218,611 discloses a method and apparatus for controlling a person's eating behavior using a counter on the table next to the food being eaten. The counter displays the number of bites to be taken at each meal, displays the actual number of bites while the bites are being taken during a meal, provides a cadence signal from which the person can pace his chewing rate, determines the size of the bite taken and the time between bites, and provides an exercise between bites which forces the person to break the eating chain by pushing a button to increment the counter.

Moreover there is known a device known as "Jaws". Said device joins the upper and lower jaws by a metal wire which is applied by a dentist. However said device is very dangerous and is not allowed for use anymore.

Today it is obvious that losing weight concerns firstly changing eating habits which is done under guidance. None of the above Patents gives a solution for said need.

Moreover in order to insert the restraining device, in some cases a helping instrument is required. A number of helping instruments such as applicators have been described as helping to insert certain devices into the oral cavity but most of them are used by the dentist (usually an orthodontist) to fix said devices on orthodontic appliances or are applicators that help the patient (usually an orthodontic patient) to put orthodontic devices in their proper brackets.

U.S. Pat. No. 5,575,643 describes an orthodontic tool wherein an elastic band can be stretched and affixed onto the hooks of an orthodontic apparatus affixed within the mouth.

U.S. Pat. No. 4,127,940A describes a dentist's instrument used to facilitate the application of an elastic arch wire-retaining band to an arch wire-supporting bracket.

U.S. Pat. No. 4,472,137A described an orthodontic instrument which is provided for attaching elastic retainer rings or bands to the brackets attached a patient's teeth.

U.S. Pat. No. 4,512,739A describes an orthodontic instrument which is designed for use by patients to help them to put and to remove the elastics on/from orthodontic hooks that are cemented on orthodontic brackets.

U.S. Pat. No. 3,475,818 describes an applicator for the placement of elastic bands on orthodontic appliances.

None of the above Patents gives a solution for the restraining device according to the present invention.

SUMMARY OF THE INVENTION

The present invention thus consists of a restraining device which is being anchored in the upper and lower jaws, consisting of an elastic element which is inserted into two respective inter-proximal spaces (IPSs) of said upper and said lower jaws and reduces and/or limits the mouth opening and/or slows down the rate of chewing.

The elastic element in accordance with the present invention may be referred to as a spring, a slab, an elastic band, an elastic rubber a cluster of fibers etc. Moreover it may be entirely, partially or partly elastic.

In a further embodiment of the present invention said restraining device i.e. the elastic element is inserted via any helping instrument such as an applicator, a retainer etc.

The applicator according to the present invention consists of at least one handle which in turn is connected to at least two arms; wherein each arm has at least one anchoring part for placing the restraining device; and wherein said handle and arms may consist as one unit.

In yet another embodiment of the present invention, restraining device i.e. the elastic element may be anchored into the two respective inter-proximal spaces (IPSs) of said upper and lower jaws respectively, via any connecting device such as orthodontic wires, hooks, implants, e.g. mini-implants in the bones of the upper jaw and the lower jaw [hereafter "connecting device"]. All of the above connecting devices may be known devices or manufactured especially for the present invention etc.

DETAILED DESCRIPTION OF THE INVENTION

The restraining device of the present invention, i.e. the elastic element in accordance with the present invention, may be an open or closed structure. Moreover, it may comprise varied and different sizes, lengths, thicknesses, and may have different shapes such as circles, squares, rectangles, ellipses, polygons etc.

However, in accordance with one embodiment of the present invention the is elastic element comprises three parts, e.g. at least one inter-dental part, at least one slow-down chewing part and at least one stopper; wherein said parts may be separate parts connected to each other or some of the parts thereof combined into one compound part.

The inter-dental part in accordance with the present invention is the part which is inserted between two adjoining teeth, e.g. IPSs, and passes through the touching points of the adjoining teeth or to the connecting device. The thickness of this part may vary in accordance with the requirement. However in one embodiment the thickness may be 0.25 mm to 1.5 mm. This part may be cut in the form of a circle, a rectangle an ellipse or the like. Said part may be made of rubber, of silicon, of nylon or may be inter-woven with cotton, with flax fibers or with any other fiber which is not elastromeric such as dental floss material or combinations thereof or may be manufactured as one component having different characteristics etc.

The inter-dental part may be either flexible or inflexible.

The stopper in accordance with the present invention is the part which is used for anchoring the restraining device i.e. the elastic element, which prevents the elastic element from being dislocated either from between the teeth or from the connecting device. Said stopper is preferably located at the ends of the restraining device, i.e. the elastic element.

Should the elastic element be open, there exist at least two stoppers (one for the upper jaw and the other for the lower jaw). However the present invention is not restricted to two stoppers only, and in another embodiment four stoppers are present in the open elastic element.

The stopper may have a triangular shape, but its geometrical shape may be triangular, circular, ring-like, disk-shaped (like a button), trapezoidal, rectangular, square, elliptical etc.

While chewing, the restraining device is stretched, at which time it pulls the stopper in such a way as to trap restraining device behind the teeth which action impedes the restraining device from coming free.

The stopper's diameter may comprise various diameters.

The stopper may be inserted between the teeth and/or placed on two adjoining teeth or on the connecting device.

The slow-down chewing part in accordance with the present invention is a flexible part which is stretched between the upper jaw and the lower jaw when opening the mouth. The dimensions of said part depend upon the force required for stopping the mouth from being opened. Said slow-down chewing part may have the form of a ring, a rectangle or any other form, either hollow or solid.

The restraining device i.e. the elastic element may be further selected from among the following possibilities. However, it is not restricted to said possibilities:

A. One open continuous element, wherein the inter-dental part and the slow-down chewing part are one unit with one stopper connected to each side.
B. One open continuous element wherein each part of the elastic element has a different thickness; wherein the slow-down chewing part is connected on both sides to the inter-dental part; and wherein each inter-dental part is connected to a stopper.
C. An elastic element as described in possibility B wherein the angle is 90° between the inter-dental part and the slow-down chewing part.
D. An elastic element as described in possibility C wherein four stoppers are present.
E. One closed continuous element like a ring.

The restraining device, i.e. the elastic element, should be manufactured from a material which fulfills at least the following conditions:

A. A strong material which cannot be torn while being inserted into the mouth.
B. A flexible material which enables the opening and closing of the mouth.

In a preferred embodiment said material is a bio-compatible material.

The restraining device, i.e. the elastic element, may have a hardness in accordance with the requirements of the rate of slow-down. In one embodiment of the present invention, the hardness is 33.2 shore, the stress is 106 kg/cm and an elongation is 865%.

The restraining device, i.e. the elastic element, may be manufactured from a range of materials, such as latex or artificial rubbers, natural or synthetic rubbers, thermoplastic polymers, polystyrene, silicon, acetyl polymers such as Delrin®, nylon resins etc. Moreover the elastic element may be made of an elastic material or of one or more springs. Furthermore, the elastic element may be interwoven from threads and different materials in order to strengthen the element and to prevent it from being torn. In yet a further embodiment, the elastic element may be made from flexible/soft materials of varying densities and a combination of the above.

The restraining device, i.e. the elastic element, may vary in diameter in different parts along the elastic element in order to control slowing down the action of opening the mouth.

Guiding the restraining device, i.e. the elastic element, into the intended crevices between the teeth i.e. the IPSs may be done using the fingers, with the user standing before a mirror if required. However in accordance with the preferred embodiment of the present invention, the restraining device, i.e. the elastic element, is inserted into its intended places with a helping instrument such as an applicator, without inserting the fingers into the mouth.

The applicator according to the present invention consists of at least one handle which in turn is connected to at least two arms; wherein each arm has at least one anchoring part for placing the restraining device; and wherein said handle and arms may consist as one unit.

The anchoring part may be any part which will anchor the device, such as a groove, a channel, a furrow, a rut, an indentation, a rough area, combinations thereof etc.

In accordance with a further embodiment of the present invention the applicator may have also pulling and releasing means, preferably pulling and releasing limb[s], which is connected to and/or part of the arm.

The applicator's handle according to the present invention serves as a grasping means for the user and/or for activating the restraining device, i.e. the elastic element.

The applicator's handle's shape enables motion, e.g. by pressing the handle it also changes its shape. In the place where the handle is connected the thickness varies to form flexibility for bending and pressing.

The applicator's handle may further have the following characters:
- The handle responds to bending activity, e.g. the purpose of the applicator is to move and to bend the arms in order to stretch the restraining device, i.e. the elastic element;
- The handle responds to pressing action;
- The handle may be comprised of different shapes which enable movement;
- The handle may be comprised of different shapes, e.g. elliptical shape, round shape, arced shape etc;
- The handle is made of stiff material or it may be made of soft material;
- The handle may be hollow or solid;
- The handle may be one closed unit or open at the end;
- The handle may be made of plastic, of metallic or of silicon material;
- The handle's thickness may continue to grow as the handle reaches the arms;
- In the handle may be parts which direct the user to the pressing point;
- The handle may be parallel to the arms or positioned at different angles such as 30°/60°/90°; and/or
- The handle is connected to the arms—the connection between the arms may be along the surface of different areas of the arms in such a configuration as an X shape.

The applicator's arms according to the present invention are used for grasping the restraining device, i.e. the elastic element. The arms may be straight or bent or in varied shapes. The shapes of the arms enable the arms to bend and to part from one another so that the restraining device, i.e. the elastic element, is stretched over two or more arms.

The applicator's arms may further have the following characteristics:
- The arms are made of stiff material, e.g. plastic, metal;
- The arms may be of different lengths;
- The arms may be of different distances one from the other; and/or
- The arms may vary in thickness, i.e. the upper part may be thicker than the lower part and vice versa. The cut of the upper arm may be made in various shapes e.g. round, rectangular, square, elliptic etc.

In one embodiment of the present invention on the arms which are close to the handle there is an anchoring part such as a groove in a different cut than in the arms that are far from the handle. Thus its shape enables the arms to bend and part from one another, e.g. the restraining device, i.e. the elastic element, is being stretched.

The anchoring parts such as grooves or rough areas of the arm according to the present invention are located at the end of the arms. Said parts serve to anchor the restraining device, i.e. the elastic element, to stretch it. The parts are found in different sizes and in different shapes, e.g. straight cut, trapezoidal cut, triangular cut, etc. The role of the parts is to anchor the restraining device, i.e. the elastic element, to the arms and to allow it to stretch.

The applicator allows the user to insert the restraining device, i.e. the elastic element, between the teeth in a comfortable and user-friendly way before the meal. After the restraining device, i.e. the elastic element, is inserted in its designated place and thereafter the applicator is removed easily.

The applicator is an instrument:
A. Which stores the restraining device, i.e. the elastic element, preferably in a stretched position, e.g. in a package, before it is being used;
B. Which assists a person in inserting the restraining device, i.e. the elastic element, into the mouth, and in positioning it where it should be, e.g. in assisting the user to insert the restraining device, i.e. the elastic element, into its place in the mouth cavity; and
C. Which assists the user in activating, e.g. in stretching a bit longer, the restraining device, i.e. the elastic element, by means of pressing a small bit upon the applicator's arms.

The applicator is made of stiff material but has flexible attributes.

The applicator may consist of one unit or more than one unit.

The device of the present invention restricts mandibular movement and therefore reduces the mouth-opening rate and slows down chewing rate of the food which is ingested. A particular aspect of the present invention is the anchoring of the device on each jaw. Because of the placement of the device, is e.g. of the elastic element, directly or via a connecting device as herein before defined in an IPS space, the anchoring of each jaw is associated directly with two adjacent teeth.

The device of the present invention is easily applied by the user with or without the intervention of any medical personnel. A user who may wish to do so, may remove the device, e.g. the elastic element, e.g. one or more worn simultaneously), at any time. Reapplication is easy and there is no limit to the number of reapplications which may be carried out. The relative comfort of the application is conducive to the tendency of a person to use the device. The use of the device of the present invention, such as the use of one or more devices, would limit bite intake, promote slow chewing and limit the absorption of food.

More particularly, the applicator and the elastic element of the present invention may be used in accordance with the following method. However, it is not restricted to said method.

A. The applicator comes with the elastic element partially expanded upon it;
B. The user grasps the applicator's handle and brings it close to his mouth;
C. The user presses on the handle which causes the elastic element to expand to its maximum capacity and enables easier preparation in order to insert the elastic element into the space between the two teeth [IPSs]; alternatively the handle is used as a handle per se; and
D. The user inserts the applicator into the mouth cavity with the elastic element expanded, e.g. pressing steadily on the handle as stated in point C. above, on the side comfortable to him, e.g. the right side or the left side; or alternatively should the handle be a handle per se, by pressing the pulling and releasing means; or combinations thereof;
E. The user bites the elastic element until it enters between the teeth by the force of the bite and locates itself between two adjacent teeth in is the upper jaw and in the lower jaw, like dental floss;
F. The user releases the pressure on the handle and in such a way frees the applicator from the restraining device, i.e. the elastic element; and
G. The user removes the applicator without the restraining device, i.e. the elastic element, from the mouth cavity.

In accordance with a preferred embodiment of the present invention, the handle is a handle per se and the elastic element is extended on the applicator. The pressing/biting actuates the pulling limb which in turn expends the elastic element further and allows it to be inserted between the teeth; with further pressing/biting, the releasing means releases the elastic means. The same pressing/biting performs both above actions.

The restraining device, i.e. the elastic element, may be removed by the following method. However it is not restricted to said method. After using the restraining device, i.e. the elastic element, the user, with the help of his finger, removes the restraining device, i.e. the elastic element, and pulls it from the mouth cavity.

The restraining device, i.e. the elastic element, may be anchored into the two respective inter-proximal spaces (IPSs) of said upper and lower jaws respectively, directly or via any connecting device such as orthodontic wires, hooks, implants, e.g. mini-implants in the bones of the upper jaw and the lower jaw (hereafter "connecting device"). All of the above connecting devices may be known devices or manufactured especially for the present invention etc. In this case the connecting device may be connected by any connecting means to an applicator such as a groove, a notch etc.

The restraining device of the present invention is to be dispensed either as a kit with separate restraining devices, i.e. elastic elements or, if desired, as a kit of with restraining devices, i.e. elastic elements and helping instruments, i.e. applicators and/or with connecting devices. By use of color coding, different sizes may be indicated and similarly, different elasticity values may be marked.

As described above, the device of the present invention promotes the restriction of food intake and therefore helps the prone individual to overcome excessive food intake.

The restraining device of the present invention may be used as an instructional and/or as a teaching instrument for alteration of eating habits by reducing and/or limiting the mouth opening and/or slowing down the rate of chewing.

The restraining device may also serve as a game for youths and teenagers, e.g. if the elastic element falls it is a sign that the youth/teenager has opened the mouth too widely and has eaten too quickly etc. The elastic element may also serve as an ornament or as a piece of jewelry, e.g. if it comes in various colors, if a gem will be mounted on the stopper or on the slowing-down part etc.

Continuous use of the restraining device of the present invention helps train the user to achieve a proper chewing rate and promotes satiety without overeating. The use of the device of the present invention promotes a direct solution to dietary problems and also promotes the prone individual to acquire proper eating habits. By applying the restraining device, the user may determine the size of the bite in such a way that a smaller amount of food is consumed in a given period of time. As a result, the user eats less and loses weight.

BRIEF DESCRIPTION OF THE DRAWINGS

The present invention will now be illustrated with reference to the accompanying drawings and examples without being limited by them. Identical parts are marked by the same numerals.

In said drawings.

DETAILED DESCRIPTION OF DRAWINGS

Figure 1:
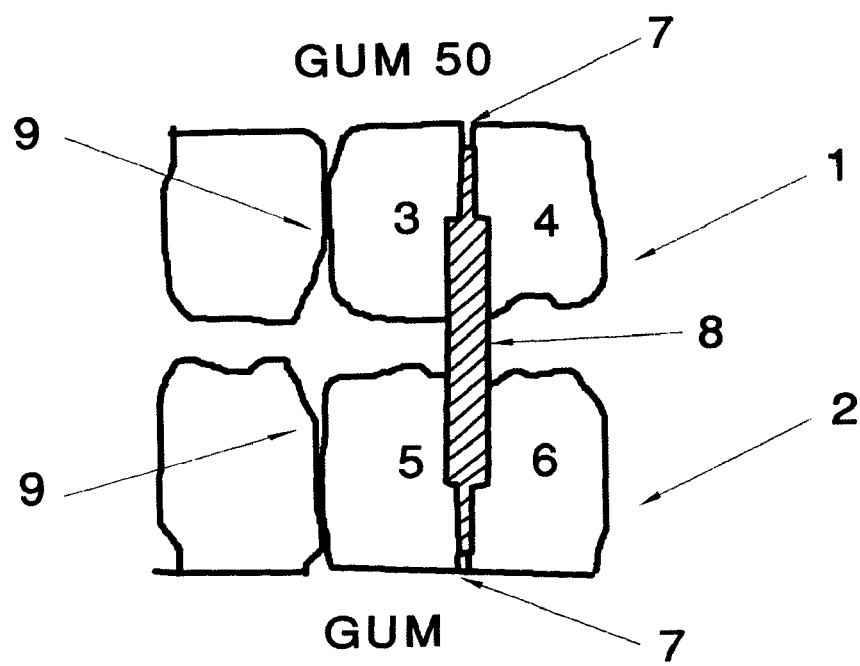
FIG. 1 is a schematic description of the oral environment in which the restraining device, i.e. the elastic element, is implemented.

The device of the present invention is a restraining device. FIG. 1 describes schematically the oral environment in which the device of the present invention is applied. The teeth in upper jaw 1 (maxilla) in a mouth are disposed in opposition to the teeth of the lower jaw (mandible) 2. In each jaw, each tooth typically forms a single contact point with an adjacent tooth on each side, allowing for a substantially triangular space limited by adjacent teeth and gum 50. Such a space is known in the art as inter-proximal space (IPS). Between tooth 3 and tooth 4, and between tooth 5 and tooth 6, two respective IPSs are indicated, namely IPS 7 and 7' respectively. Restraining device 8, namely the elastic element as applied, is described schematically in FIG. 1.

Device 8 is inserted between two adjacent teeth in upper jaw 1 and two adjacent teeth in lower jaw 2 through contact point 9.

Several versions of device 8, namely of the elastic elements, is shown in FIGS. 2A, 2B, 2C, 2D and 2E.

Figure 2A:
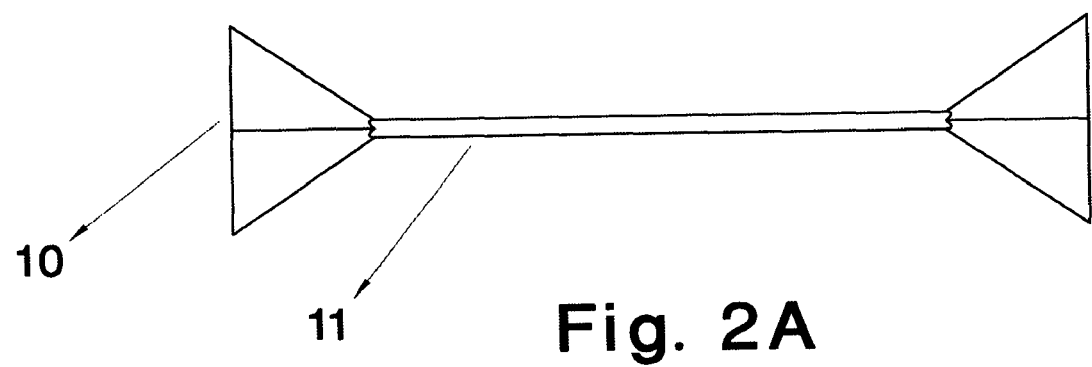
FIG. 2A is a schematic side description of the restraining device, i.e. the elastic element.
Figure 2B:
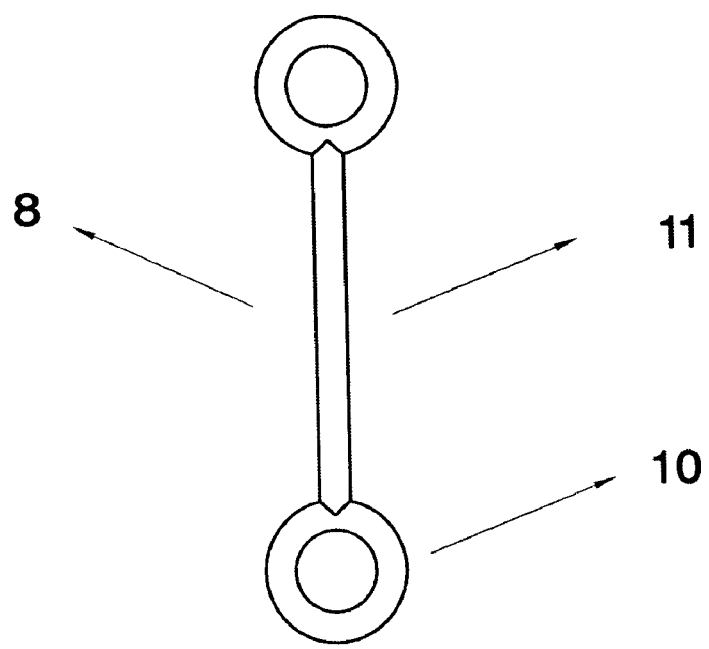
FIG. 2B is a schematic side description of another restraining device, i.e. the elastic element, in accordance with the present invention.
Figure 2C:
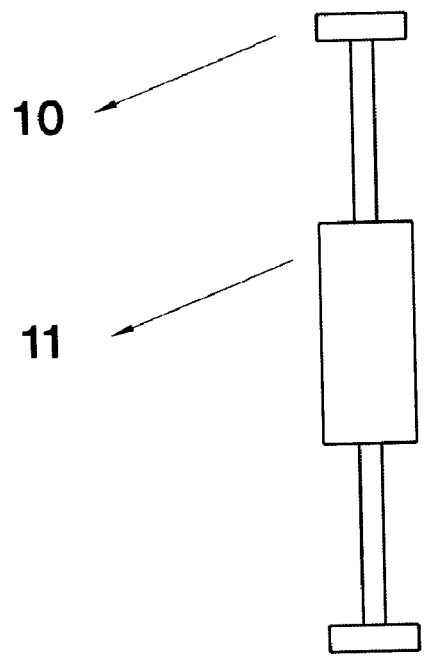
FIG. 2C is a schematic side description of another restraining device, i.e. the elastic element, in accordance with the present invention.
Figure 2D:
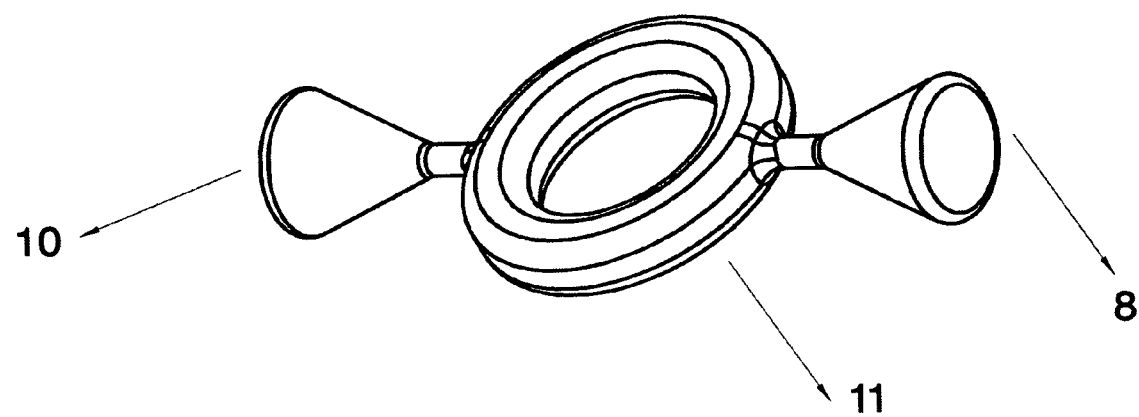
FIG. 2D is a schematic perspective description of another restraining device, i.e. the elastic element, in accordance with the present invention.
Figure 2E:
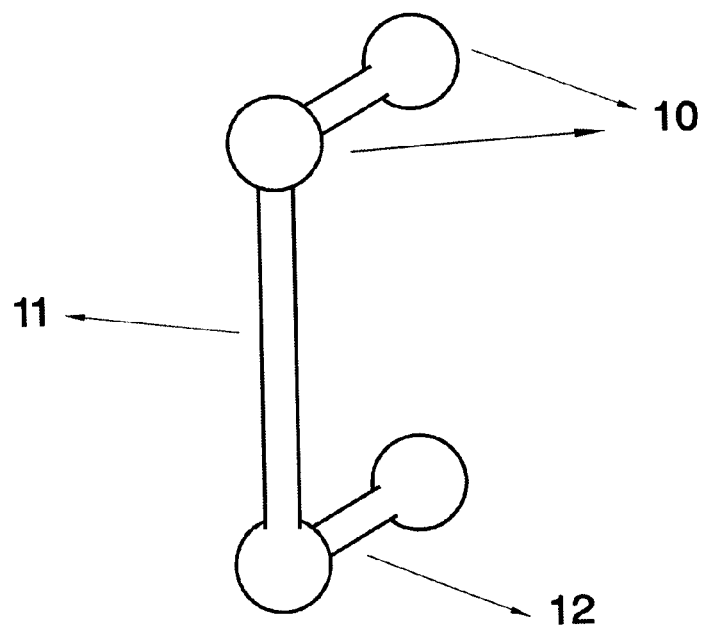
FIG. 2E is a schematic side description of another restraining device, i.e. the elastic element, in accordance with the present invention.

In FIGS. 2A, 2B, 2C and 2D is shown device 8 comprising two stoppers 10 which are connected by slow-down chewing part 11. In FIG. 2B, stopper 10 has the form of a ring. In FIGS. 2C and 2D slow-down chewing part 11 has varying widths. In FIGS. 2A, 2B, 2C and 2D slow-down chewing part 11 consists also of the inter-dental part. In FIG. 2E are shown four stoppers 10 wherein each pair of stoppers 10 are connected to one another by inter-dental part 12.

Figure 3:
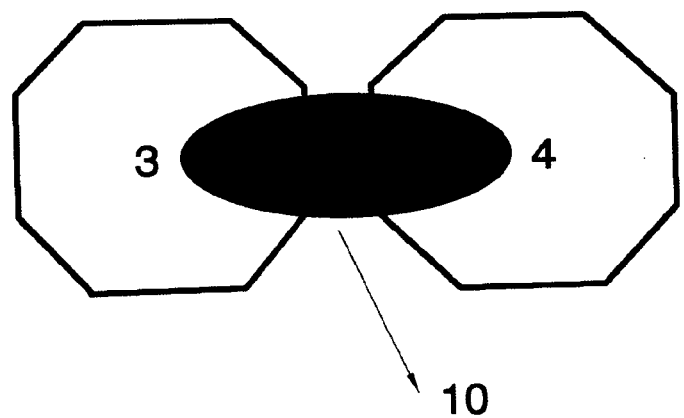
FIG. 3 shows two adjacent teeth having the restraining device, i.e. the elastic element, stopper, between them.

FIG. 3 shows two adjacent teeth, tooth 3 and tooth 4, having between them stopper 10 of device 8.

Figure 4:
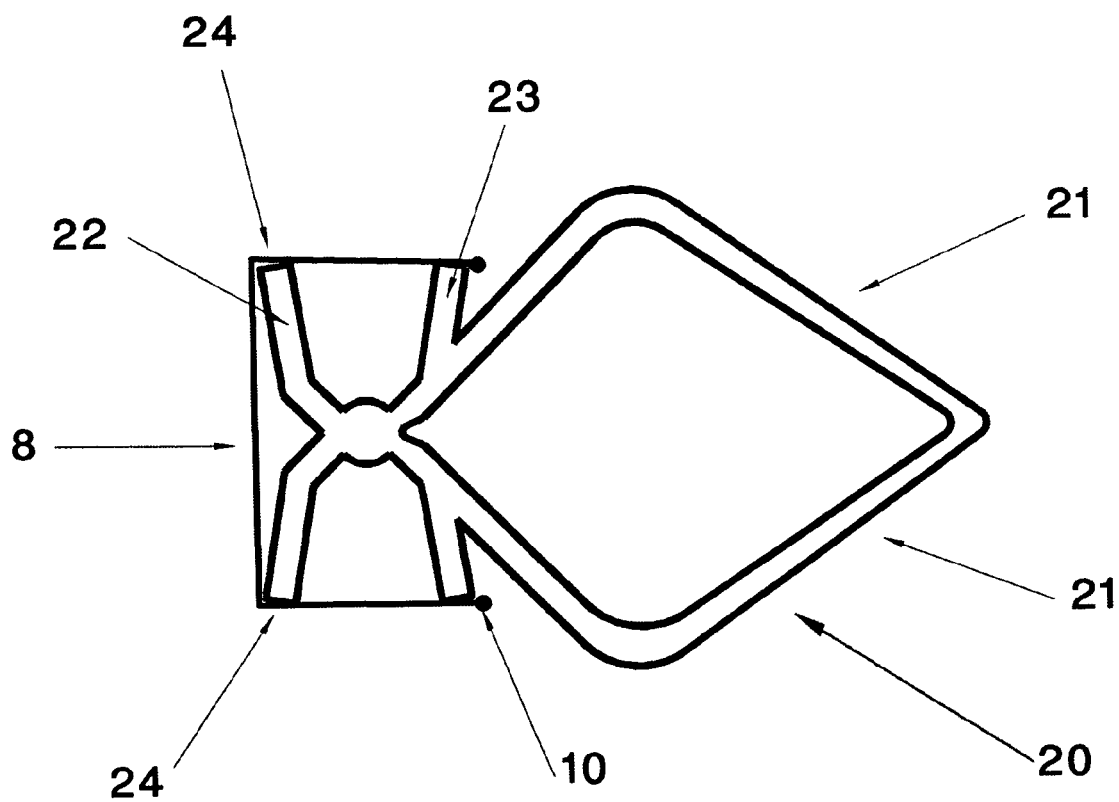
FIG. 4 is a schematic side description of the applicator in accordance with the present invention having the restraining device, i.e. the elastic element.

FIG. 4 shows applicator 20 by itself when it is attached to device 8. Applicator 20 comprises handle 21, which in turn is connected to arms 22 and 23. Grooves 24 are located at the ends of both arms 22 and 23 and serve to hold device 8 in place so that it will not be harmed. Another purpose of handle 21 is to stretch device 8. After the user bites down on the part of device 8 located between arms 22 and 23, the user removes applicator 20 from his mouth.

Figure 5:
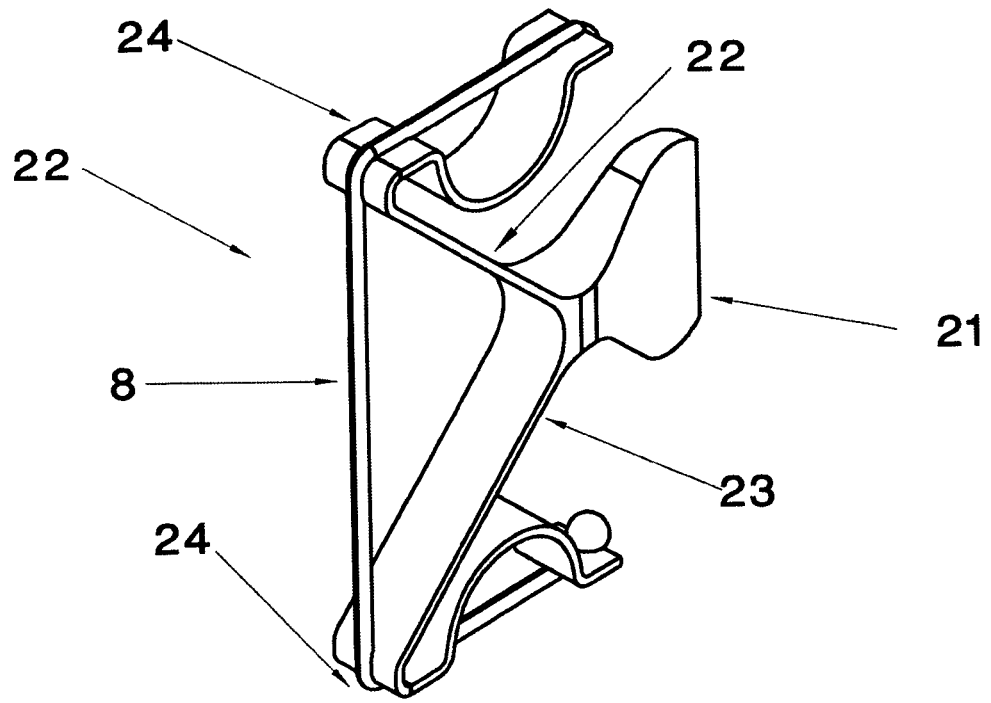
FIG. 5 is a schematic perspective description of another applicator in accordance with the present invention having the restraining device, i.e. the elastic element.

FIG. 5 shows another applicator 20 with device 8 stretched upon it, which comprises arms 22 and 23 having at their ends grooves 24 assembled side by side rather than one in front and one in back. During use, biting on device 8 brings arms 22 and 23 closer together and as a result device 8 is stretched. After the bite the user removes applicator 20 and the device 8 stays between the teeth.

Figure 6:
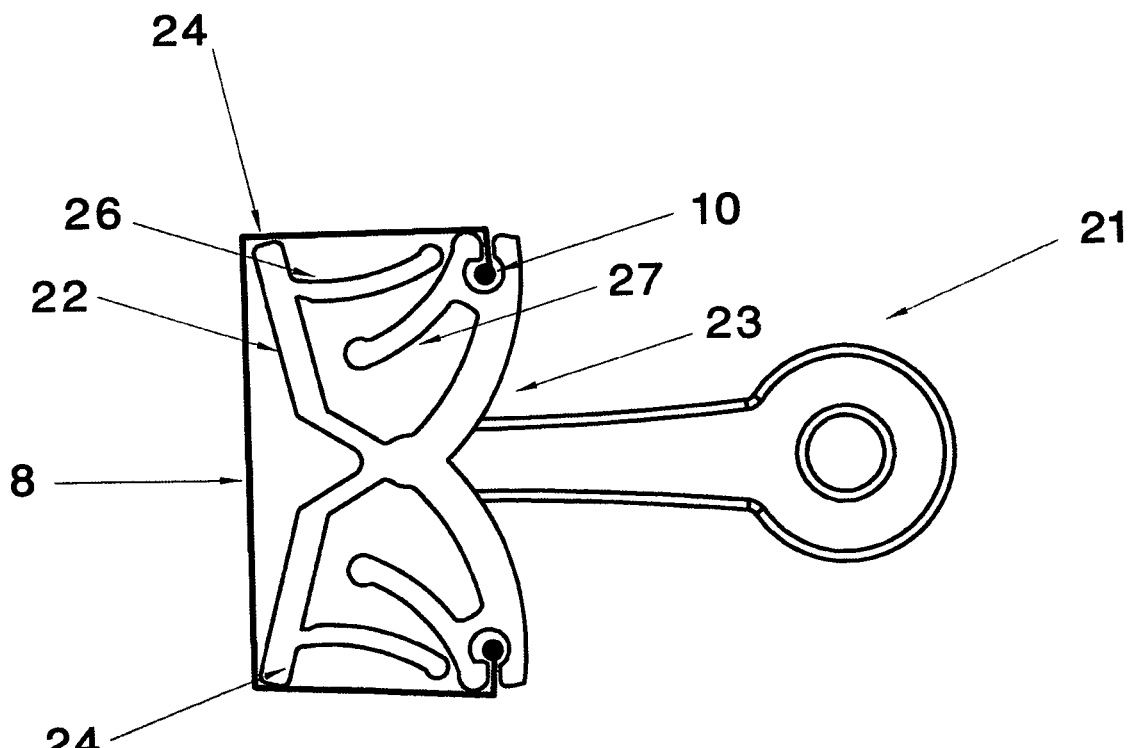
FIG. 6 is a schematic perspective description of another applicator before use, in accordance with the present invention having the restraining device, i.e. the elastic element.

FIG. 6 shows another applicator 20 before use with device 8 stretched upon it. Said applicator 20 has only one handle 21 which is not meant to operate device 8 but only to hold it. Said handle 21 is connected to arms 22 and 23.

Arm 22 in turn and arm 23 in turn have pulling limb 26 and releasing limb 27. Pulling limb 26 serves for stretching device 8 and releasing limb 27 serves for releasing it.

After the user bites down on device 8, pulling limb 26 stretches device 8 in order to insert it between the teeth (not shown). When pulling limb 26 descends, it activates releasing limb 27 which releases device 8 from applicator 20 and makes it possible to remove applicator 20 from the mouth while device 8 remains between the upper and lower jaws.

Figure 7:
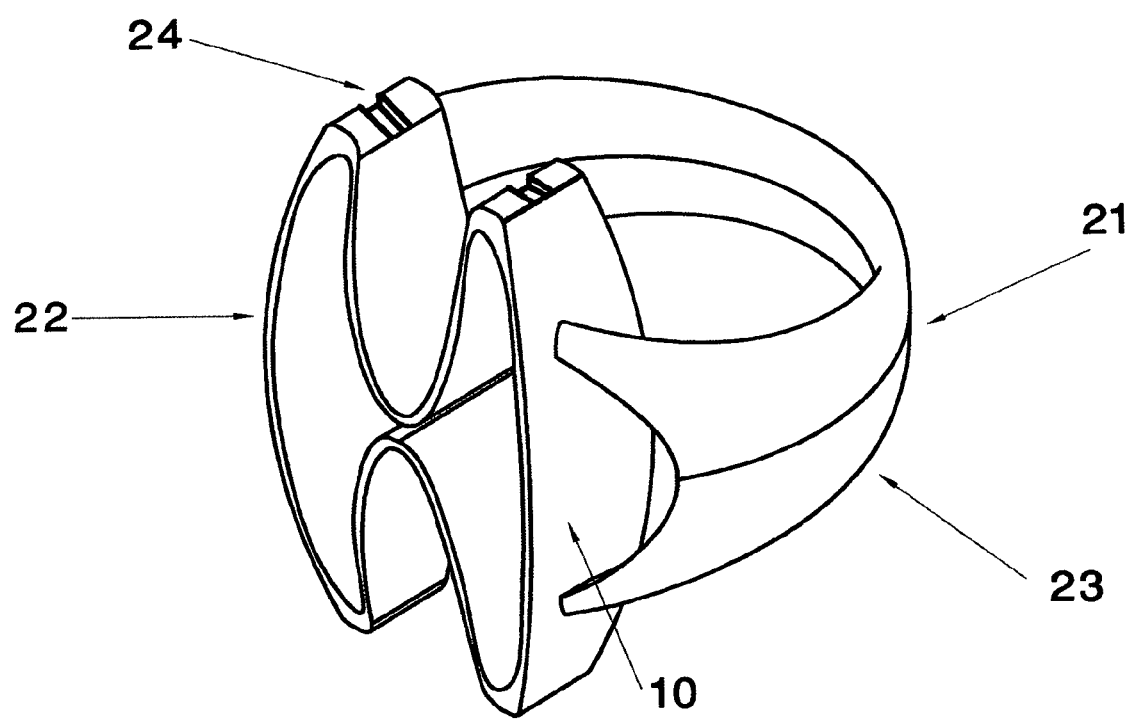
FIG. 7 is a schematic perspective description of another applicator in accordance with the present invention.

FIG. 7 shows another applicator 20 alone without device 8 (not shown), having handle 21 which is substantially 90° to arms 22 and 23 having at their upper side grooves 24. Said applicator 20 is inserted into the mouth from the front whereas applicator 20 in other figures is inserted from the side. When pressing arms 22 and 23 they are drawn closer together and as a result device 8 (not shown) is stretched.

The invention claimed is:

1. A restraining device comprising:
    an elastic element adapted to be inserted into two respective inter-proximal spaces (IPSs) of an upper jaw and a lower jaw to reduce and/or limit a mouth opening and/or slow down a rate of chewing, wherein the device is adapted to be anchored in the upper jaw and the lower jaw;
    wherein the elastic element is selected from among the following forms:
    A. one open continuous element, wherein the inter-dental part and the slow-down chewing part are one unit with one stopper connected to each side;
    B. one open continuous element wherein each part of the elastic element has a different thickness; wherein the slow-down chewing part is connected on both sides to the inter-dental part; and wherein each inter-dental part is connected to a stopper;
    C. an elastic element as claimed in possibility B wherein the angle is 90° between the inter-dental part and the slow-down chewing part;
    D. an elastic element as claimed in possibility C wherein four stoppers are present; and
    E. one closed continuous element.

2. The restraining device according to claim 1, wherein the elastic element includes at least one of, a spring, a slab, an elastic band, an elastic rubber or a cluster of fibers, and is entirely, partially or partly elastic.

3. The restraining device according to claim 1, wherein the elastic element comprises the following parts:
    at least one inter-dental part;
    at least one slow-down chewing part; and
    at least one stopper,
    wherein said parts are separate parts connected to each other or one or more of the parts are combined into one compound part.

4. The restraining device according to claim 1, wherein the elastic element is manufactured from a material including:
    a strong material which cannot be torn while being inserted into the mouth; and
    a flexible material which enables the opening and closing of the mouth.

5. The restraining device according to claim 4, wherein the elastic material is a bio-compatible material.

6. The restraining device according to claim 4, wherein the elastic element is manufactured from a range of materials, selected among latex or artificial rubbers, natural or synthetic rubbers, thermoplastic polymers, polystyrene, silicon and acetyl polymers selected among Delrin® and nylon resins.

7. The restraining device according to claim 1, wherein the elastic element is inserted via a helping instrument selected between either an applicator or a retainer.

8. The restraining device according to claim 7, wherein the applicator comprises:
    at least one handle which in turn is connected to at least two arms, wherein each arm has at least one anchoring part for placing the restraining device.

9. The restraining device according to claim 8, wherein the anchoring part includes at least one of, a groove, a channel, a furrow, a rut, an indentation, a rough area, or a combination thereof.

10. The restraining device according to claim 8, wherein the applicator has a pulling and releasing element.

11. The restraining device according to claim 10, wherein the pulling and releasing element is a limb which is connected to and/or part of the arm.

12. The restraining device according to claim 8, wherein the applicator is made of a stiff material but has flexible attributes.

13. The restraining device according to claim 8, wherein the applicator comprises one unit or more than one unit.

14. The restraining device as defined in claim 7, wherein the applicator comprises a handle having at least two arms, each arm having at least one anchoring part for placing the restraining device, wherein said handle and arms comprise one unit, and wherein the elastic element is anchored into the two respective inter-proximal spaces (IPSs) of the upper and lower jaws respectively, via a connecting device selected among orthodontic wires, hooks, and implants in the bones of the upper and lower jaws.

15. The restraining device according to claim 1, wherein the restraining device is connected to a helping instrument.

16. The restraining device according to claim 1, wherein the elastic element is anchored into the two respective inter-proximal spaces (IPSs) of the upper and lower jaws respectively, via a connecting device selected among orthodontic wires, hooks, and implants in the bones of the upper and lower jaws.

17. The restraining device according to claim 1, wherein the elastic element comprises:
  an upper inter-dental part configured to be placed in the inter-proximal space of the upper jaw;
  a lower inter-dental part configured to be placed in the inter-proximal space of the lower jaw;
  a slow-down chewing part connecting the upper and lower inter-dental parts; and
  two stoppers connected to each end of the upper and lower inter-dental parts.

18. The restraining device according to claim 17, wherein the slow-down chewing part has a varying width over its length.

19. The restraining device according to claim 18, wherein the slow-down chewing part comprises a closed continuous element.

20. The restraining device according to claim 17, further comprising two other stoppers, each of which being located between the slow-down chewing part and the upper and lower inter-dental parts respectively, wherein each of the upper and lower inter-dental parts extends from the slow-down chewing part with an angle including 90°.

21. A method for using a restraining device comprising an elastic element which is a bio-compatible material, wherein the elastic element is anchored into two respective inter-proximal spaces (IPSs) of an upper and a lower jaws respectively, via a connecting device selected among orthodontic wires, hooks, and implants in the bones of the upper and lower jaws, the method comprising:

A. The applicator comes with the restraining device partially expanded upon it;
  B. The user grasps the applicator's handle and brings it close to his mouth;
  C. The user presses on the handle which causes the elastic element to expand to its maximum capacity and enables easier preparation in order to insert the elastic element into the space between the two teeth (IPSs); alternatively the handle is used as a handle per se; and
  D. The user inserts the applicator into the mouth cavity with the elastic element expanded, e.g. pressing steadily on the handle as stated in point C. above, on the side comfortable to him, e.g. the right side or the left side; or alternatively should the handle be a handle per se, by pressing the pulling and releasing means; or combinations thereof;
  E. The user bites the restraining device until it enters between the teeth by the force of the bite and locates itself between two adjacent teeth in the upper and lower jaws;
  F. The user releases the pressure and thus the applicator is freed from the restraining device; and
  G. The user removes the applicator without the restraining device from the mouth cavity.

22. The method according to claim 21, wherein the user, with the help of his finger, removes the restraining device and pulls it from the mouth cavity.

23. A method for restraining movement of the jaw comprising:
  providing a restraining device comprising:
    inserting an elastic element adapted to be inserted into a first inter-proximal space (IPS) of an upper jaw;
    inserting and a second inter-proximal space (IPS) a lower jaw to at least one of, reduce and limit a mouth opening and slow down a rate of chewing,
    wherein the elastic element has a first end and a second end;
    positioning the first end of the elastic element in the first inter-proximal space (IPS) of the upper jaw;
    positioning the second end of the elastic element in the first inter-proximal space (IPS) of the lower jaw; and
    the device is adapted to be anchored in the upper jaw and the lower jaw by the positioning of the first end of the elastic element in the first inter-proximal space (IPS) of the upper jaw and the positioning of the second end of the elastic element to the second inter-proximal space (IPS) of the lower jaw;
  positioning of the first end of the elastic element in the first inter-proximal space (IPS) of the upper jaw and the positioning of the second end of the elastic element in the second inter-proximal space (IPS) of the lower jaw, thereby restraining movement of the jaw.

* * * * *

UNITED STATES PATENT AND TRADEMARK OFFICE
CERTIFICATE OF CORRECTION

PATENT NO.       : 8,375,954 B2                                           Page 1 of 1
APPLICATION NO. : 12/808364
DATED            : February 19, 2013
INVENTOR(S)      : Erella Pines It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 174 days.

Signed and Sealed this
First Day of September, 2015

Michelle K. Lee
*Director of the United States Patent and Trademark Office*